(12) United States Patent
Iwashita et al.

(10) Patent No.: US 11,303,831 B2
(45) Date of Patent: Apr. 12, 2022

(54) RADIATION IMAGING APPARATUS AND RADIATION IMAGING METHOD

(71) Applicant: CANON KABUSHIKI KAISHA, Tokyo (JP)

(72) Inventors: Atsushi Iwashita, Tokyo (JP); Kosuke Terui, Yokohama (JP); Akira Tsukuda, Kawasaki (JP); Sota Torii, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 356 days.

(21) Appl. No.: 16/519,456

(22) Filed: Jul. 23, 2019

(65) Prior Publication Data
US 2019/0349541 A1 Nov. 14, 2019

Related U.S. Application Data

(63) Continuation of application No. PCT/JP2018/003771, filed on Feb. 5, 2018.

(30) Foreign Application Priority Data

Feb. 10, 2017 (JP) .............................. JP2017-023474

(51) Int. Cl.
*H04N 5/335* (2011.01)
*H04N 5/363* (2011.01)
(Continued)

(52) U.S. Cl.
CPC ............. *H04N 5/363* (2013.01); *H04N 5/343* (2013.01); *H04N 5/353* (2013.01); *H04N 5/378* (2013.01)

(58) Field of Classification Search
CPC ........ H04N 5/343; H04N 5/353; H04N 5/363; H04N 5/378
See application file for complete search history.

(56) References Cited

U.S. PATENT DOCUMENTS 6,947,084 B2    9/2005  Kaifu et al.
8,985,853 B2 *  3/2015  Lee ......................... G01T 7/005
                                                              378/207
(Continued)

FOREIGN PATENT DOCUMENTS

JP    2002-051265    2/2002
JP    2009-504221    2/2009
(Continued)

OTHER PUBLICATIONS

U.S. Appl. No. 16/460,083, Takeshi Noda, Filing Date Jul. 2, 2019.

*Primary Examiner* — Kevin K Pyo
(74) *Attorney, Agent, or Firm* — Venable LLP

(57) ABSTRACT

A radiation imaging apparatus includes an imaging unit having a pixel array of pixels, and a signal processing unit for processing a signal from the imaging unit. Each pixel includes a conversion element for converting radiation into electrical signal and a reset unit for resetting the conversion element, the signal processing unit generates radiation image based on first image corresponding to electrical signal converted by the conversion unit of each pixel in a first period, and second image corresponding to electrical signal converted by the conversion element of each pixel in a second period which starts after start of the first period and ends before end of the first period, and in each pixel, the conversion element is not reset by the reset unit in the first period.

15 Claims, 12 Drawing Sheets

(51) Int. Cl.
    *H04N 5/343* (2011.01)
    *H04N 5/353* (2011.01)
    *H04N 5/378* (2011.01)

(56) References Cited

U.S. PATENT DOCUMENTS

| | | |
|---|---|---|
| 9,048,154 B2 | 6/2015 | Takenaka et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,812,474 B2 | 11/2017 | Yagi et al. |
| 9,820,711 B2 | 11/2017 | Tsukuda |
| 9,971,046 B2 | 5/2018 | Ryu et al. |
| 9,980,685 B2 | 5/2018 | Iwashita et al. |
| 9,989,656 B2 | 6/2018 | Sato et al. |
| 10,009,990 B2 | 6/2018 | Takenaka et al. |
| 10,070,082 B2 | 9/2018 | Tsukuda |
| 10,197,684 B2 | 2/2019 | Terui et al. |
| 10,274,612 B2 | 4/2019 | Ishii et al. |
| 10,441,238 B2 | 10/2019 | Terui et al. |
| 2002/0024601 A1 | 2/2002 | Kaifu |
| 2008/0232549 A1 | 9/2008 | Poorter |
| 2012/0075515 A1 | 3/2012 | Dowaki |
| 2012/0087471 A1 | 4/2012 | Naito |
| 2014/0239186 A1 | 8/2014 | Sato et al. |
| 2014/0361189 A1 | 12/2014 | Kameshima et al. |
| 2015/0131785 A1 | 5/2015 | Topfer |
| 2016/0131772 A1 | 5/2016 | Sato |
| 2016/0270755 A1 | 9/2016 | Takenaka et al. |
| 2016/0363674 A1 | 12/2016 | Jacob |
| 2018/0128755 A1 | 5/2018 | Iwashita et al. |
| 2018/0317868 A1 | 11/2018 | Terui et al. |
| 2018/0328862 A1 | 11/2018 | Sato et al. |
| 2019/0179036 A1 | 6/2019 | Takenaka et al. |
| 2020/0150286 A1* | 5/2020 | Terui ............... H04N 5/378 |

FOREIGN PATENT DOCUMENTS

| | | |
|---|---|---|
| JP | 2012-125409 A | 7/2012 |
| JP | 2013-219751 | 10/2013 |
| JP | 2014-090960 | 5/2014 |
| WO | 03/016831 A1 | 2/2003 |
| WO | 2007/017773 | 2/2007 |

* cited by examiner

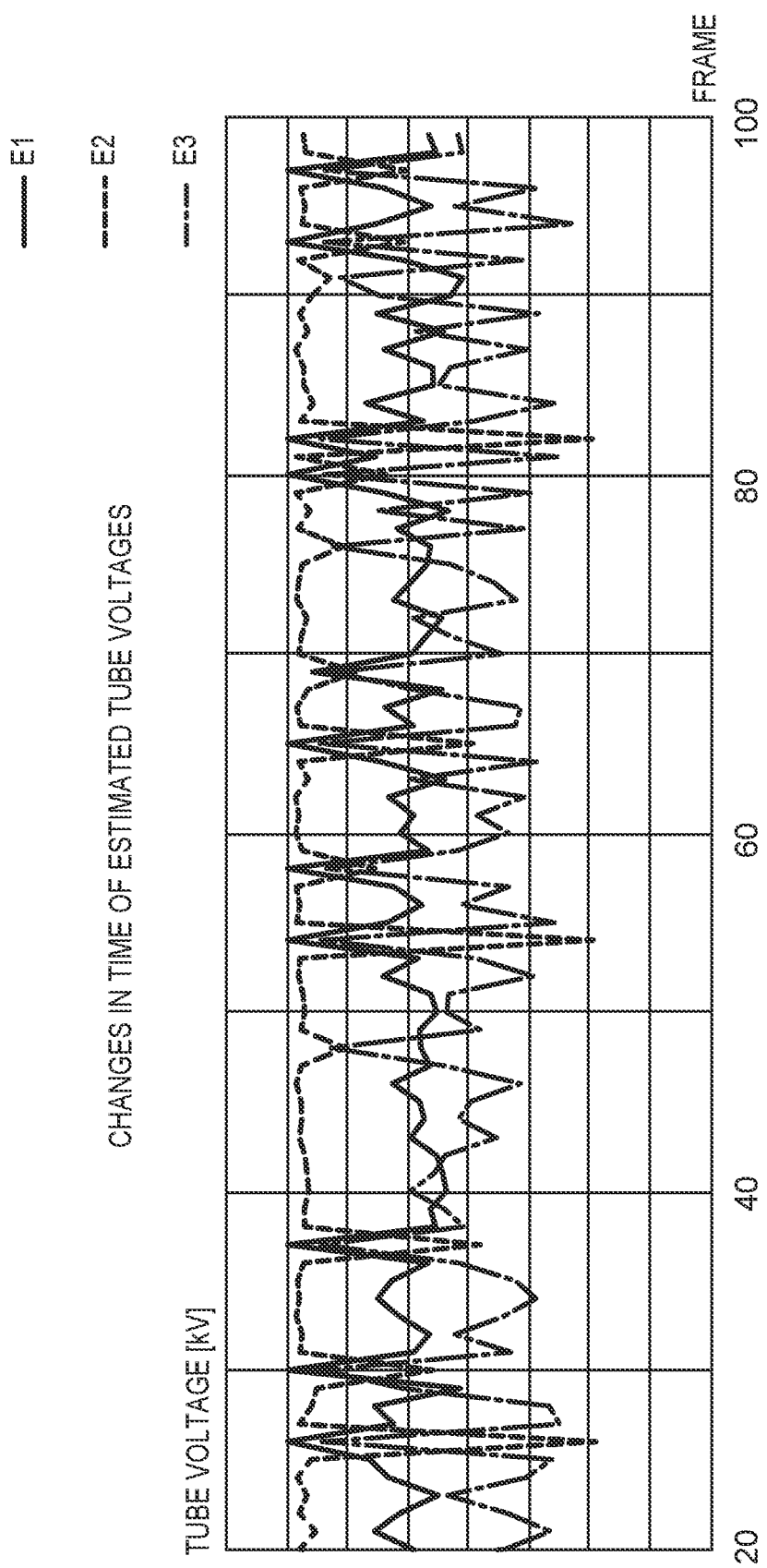

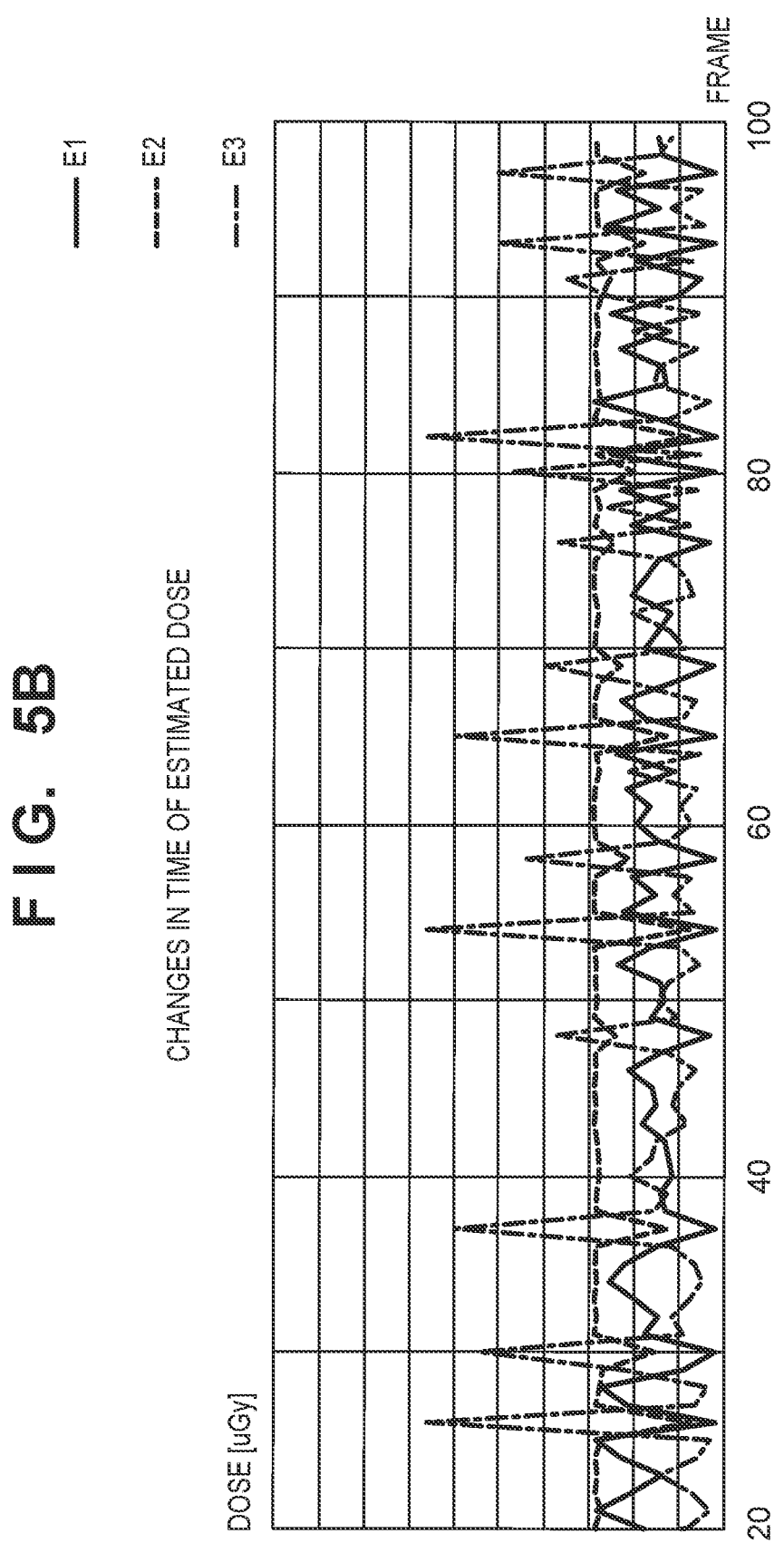

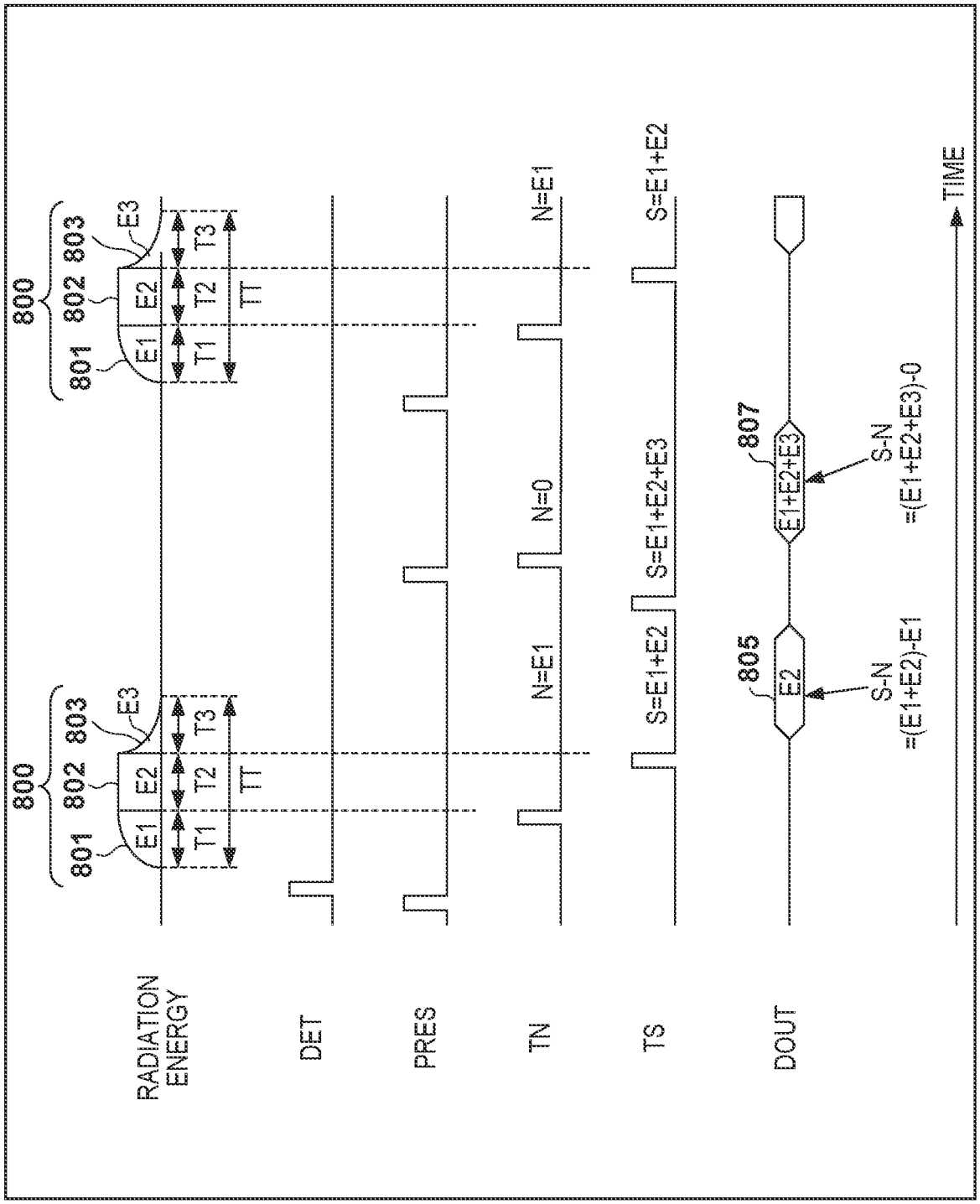

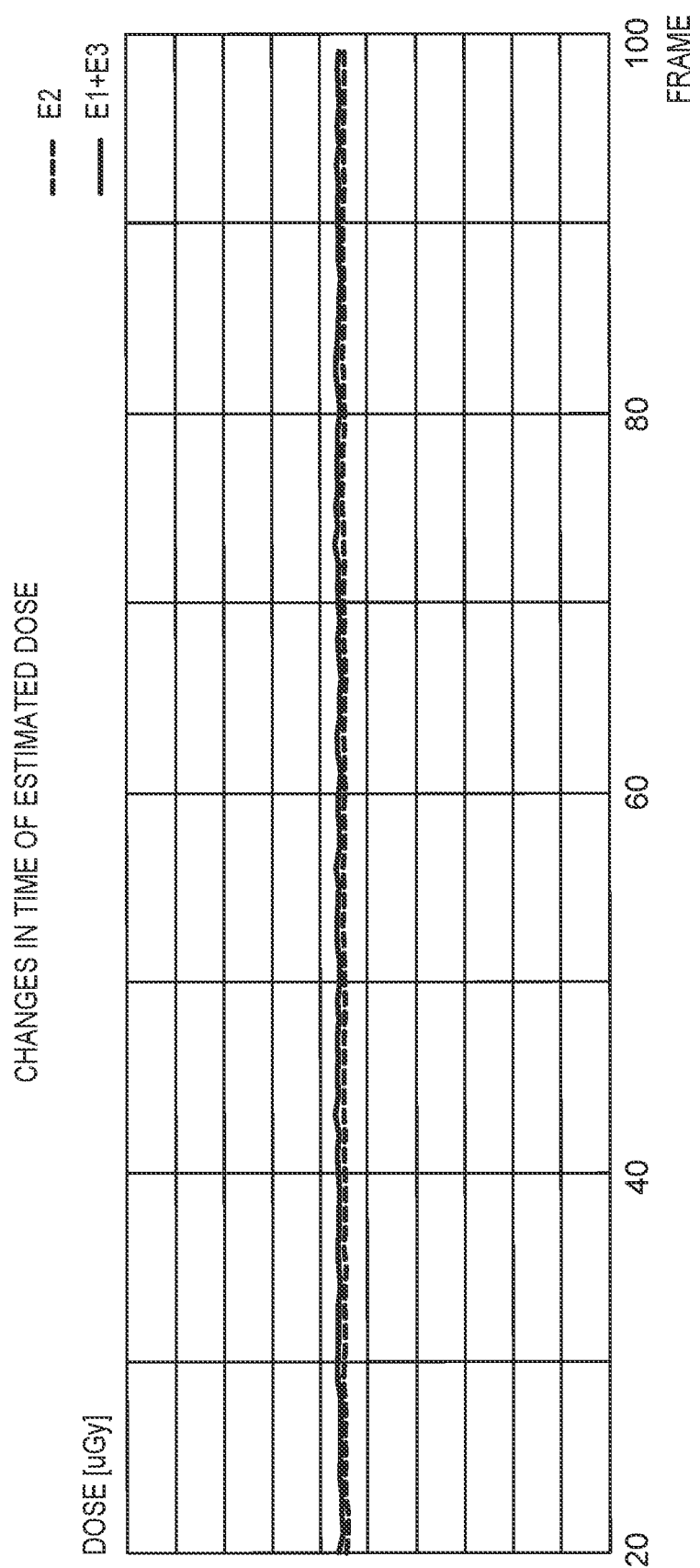

RADIATION IMAGING APPARATUS AND RADIATION IMAGING METHOD

CROSS-REFERENCE TO RELATED APPLICATIONS

This application is a Continuation of International Patent Application No. PCT/JP2018/003771, filed Feb. 5, 2018, which claims the benefit of Japanese Patent Application No. 2017-023474, filed Feb. 10, 2017, both of which are hereby incorporated by reference herein in their entirety.

BACKGROUND OF THE INVENTION

Field of the Invention

The present invention relates to a radiation imaging apparatus and a radiation imaging method.

Background Art

There is an energy subtraction method as an imaging method that applies a radiation imaging apparatus. The energy subtraction method is a method of obtaining new images (for example, a bone image and a soft tissue image) by processing a plurality of images obtained by capturing an object a plurality of times while changing energy of radiation to irradiate the object. A time interval during which a plurality of radiation images are captured is, for example, several seconds or more in a radiation imaging apparatus to capture a still image, about 100 msec in a general radiation imaging apparatus for a moving image, and about 10 msec even in a radiation imaging apparatus for a high-speed moving image. If the object moves in this time interval, an artifact is caused by that movement. It is therefore difficult to obtain, by the energy subtraction method, a radiation image of an object such as a heart that moves fast.

Japanese Patent Laid-Open No. 2009-504221 describes a system that performs dual energy imaging. In this system, the tube voltage of an X-ray source is set to the first kV value, and then changed to the second kV value in imaging. Then, the first signal corresponding to the first sub-image is integrated when the tube voltage is the first kV value, and integration is reset after the integrated signal is transferred to a sample and hold node. Subsequently, the second signal corresponding to the second sub-image is integrated when the tube voltage is the second kV value. Consequently, readout of the integrated first signal and integration of the second signal are performed in parallel.

A method described in Japanese Patent Laid-Open No. 2009-504221 performs readout of the integrated first signal and integration of the second signal in parallel, making it possible to shorten a time interval during which two images for the energy subtraction method are captured. In the method described in Japanese Patent Laid-Open No. 2009-504221, however, a reset operation exists after integration and transfer of the first signal corresponding to the first sub-image in order to obtain two radiation images (the first sub-image and the second sub-image). When a radiation irradiation time is shortened up to about 1 msec in order to suppress the influence of an object movement, the object is irradiated with radiation wastefully for a time at 10 percent of the radiation irradiation time even if the reset operation can be completed in 0.1 msec.

SUMMARY OF INVENTION

The present invention has been made in response to the above problem recognition and has as its object to provide a technique advantageous in reducing the irradiation of radiation which does not contribute to imaging and obtaining a radiation image within a shorter time.

An aspect of the present invention relates to a radiation imaging apparatus comprising an imaging unit including a pixel array including a plurality of pixels and a signal processing unit configured to process a signal from the imaging unit, wherein each of the plurality of pixels includes a conversion element configured to convert radiation into an electrical signal and a reset unit configured to reset the conversion element, the signal processing unit generates a radiation image based on a first image corresponding to an electrical signal converted by the conversion unit of each of the plurality of pixels in a first period and a second image corresponding to an electrical signal converted by the conversion element of each of the plurality of pixels in a second period which starts after a start of the first period and ends before an end of the first period, and in each of the plurality of pixels, the conversion element is not reset by the reset unit in the first period.

Further features of the present invention will become apparent from the following description of exemplary embodiments with reference to the attached drawings.

BRIEF DESCRIPTION OF DRAWINGS

FIG. 5A is a graph for explaining a variation between the frames of a radiation image;

FIG. 5B is a graph for explaining a variation between the frames of a radiation image;

FIG. 8 is a timing chart showing an example of the operation of the radiation imaging apparatus in an extension mode 3;

FIG. 9B is a graph for explaining an effect of reducing a variation between the frames of a radiation image.

DESCRIPTION OF EMBODIMENTS

A preferred embodiment of the present invention will be explained below with reference to the accompanying drawings.

Figure 1:
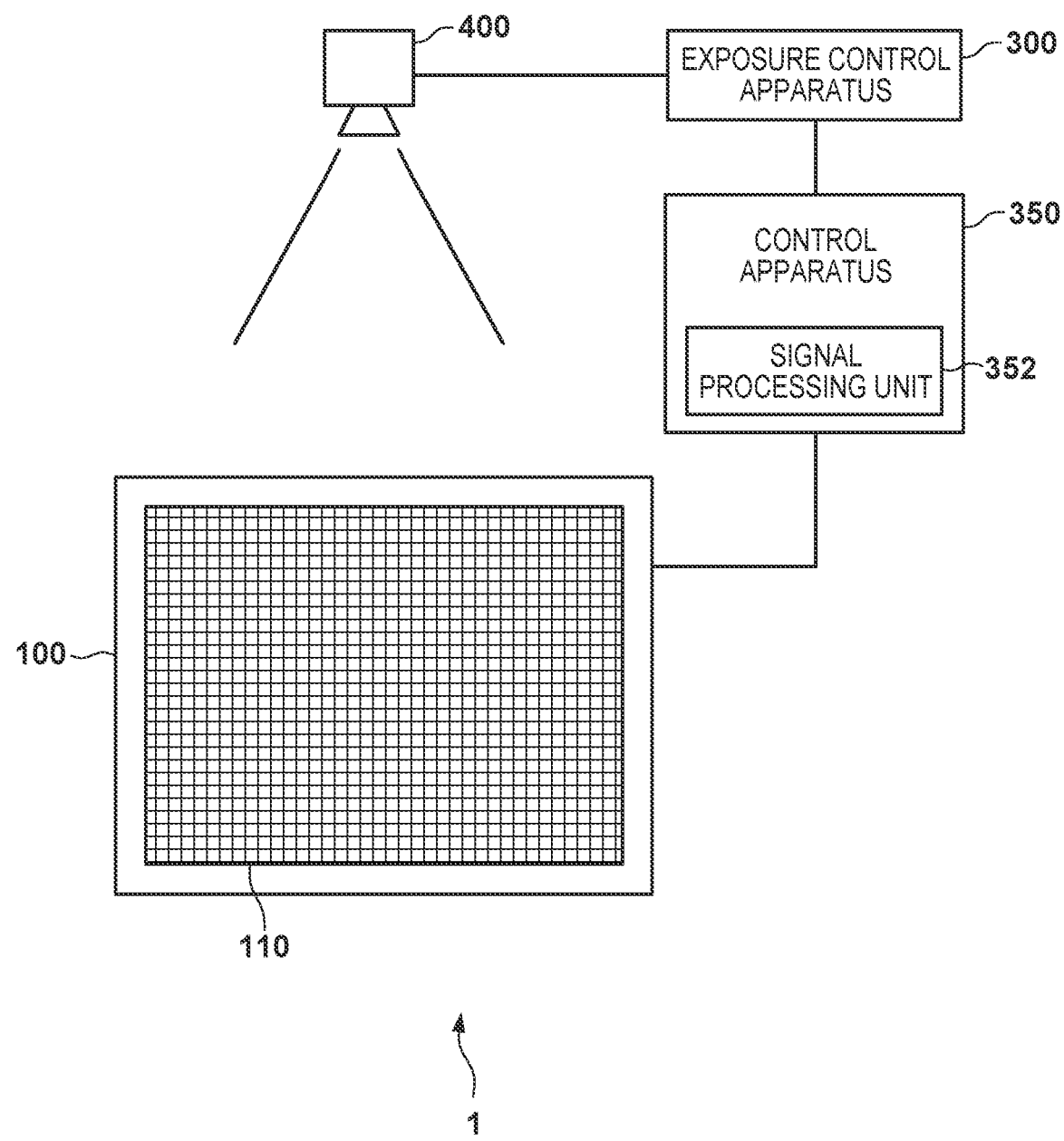
FIG. 1 is a diagram showing the arrangement of a radiation imaging apparatus according to an embodiment of the present invention.

FIG. 1 shows the arrangement of a radiation imaging apparatus 1 according to an embodiment of the present invention. The radiation imaging apparatus 1 can include an imaging unit 100 including a pixel array 110 including a plurality of pixels and a signal processing unit 352 that processes a signal from the imaging unit 100. The imaging unit 100 can have, for example, a panel shape. As exemplified in FIG. 1, the signal processing unit 352 may be arranged as part of a control apparatus 350, incorporated in the same housing as the imaging unit 100, or incorporated in a housing different from that of the imaging unit 100 and the control apparatus 350. The radiation imaging apparatus 1 is an apparatus for obtaining a radiation image by an energy subtraction method. The energy subtraction method is a method of obtaining new radiation images (for example, a bone image and a soft tissue image) by processing a plurality of images obtained by capturing an object a plurality of times while changing energy of radiation to irradiate the object. The term "radiation" can include, for example, α-rays, β-rays, γ-rays, particle rays, and cosmic rays in addition to X-rays.

The radiation imaging apparatus 1 can include a radiation source 400 that generates radiation, an exposure control apparatus 300 that controls the radiation source 400, and the control apparatus 350 that controls the exposure control apparatus 300 (the radiation source 400) and the imaging unit 100. The control apparatus 350 can include a signal processing unit 352 that processes a signal supplied from the imaging unit 100 described above. All or some functions of the control apparatus 350 can be incorporated in the imaging unit 100. Alternatively, some functions of the imaging unit 100 can be incorporated in the control apparatus 350. The control apparatus 350 can be formed by a computer (processor) and a memory that stores programs provided for the computer. The signal processing unit 352 can be made of some of the programs. Alternatively, the signal processing unit 352 can be made of a computer (processor) and a memory that stores programs provided for the computer. The control apparatus 350 may be formed by a DSP (digital signal processor) or a PLA (programmable logic array) entirely or partially. The control apparatus 350 and the signal processing unit 352 may be designed and manufactured by a logic synthesis tool based on a file that describes their operations.

The exposure control apparatus 300 can include, for example, an exposure switch and in response to the fact that the exposure switch is turned on, cause the radiation source 400 to emit radiation and notify the control apparatus 350 of information indicating a timing at which the radiation is emitted. Alternatively, the exposure control apparatus 300 causes the radiation source 400 to emit radiation in accordance with a command from the control apparatus 350.

The radiation whose energy (wavelength) changes in a continuous radiation period of the radiation can be emitted from the radiation source 400. By using such radiation, radiation images are obtained at two different energies, and these radiation images are processed by the energy subtraction method, thereby obtaining a new radiation image. Alternatively, the radiation source 400 may have a function of changing radiation energy (wavelength). The radiation source 400 can have a function of changing the radiation energy by changing, for example, a tube voltage (a voltage applied between the cathode and anode of the radiation source 400).

Each of the plurality of pixels forming the pixel array 110 of the imaging unit 100 includes a conversion unit that converts radiation into an electrical signal (for example, charges) and a reset unit that resets the conversion unit. Each pixel may be configured to convert the radiation into the electrical signal directly or may be configured to convert the radiation into light such as visible light, and then convert the light into the electrical signal. In the latter case, a scintillator for converting radiation into light can be used. The plurality of pixels that form the pixel array 110 can share the scintillator.

Figure 2:
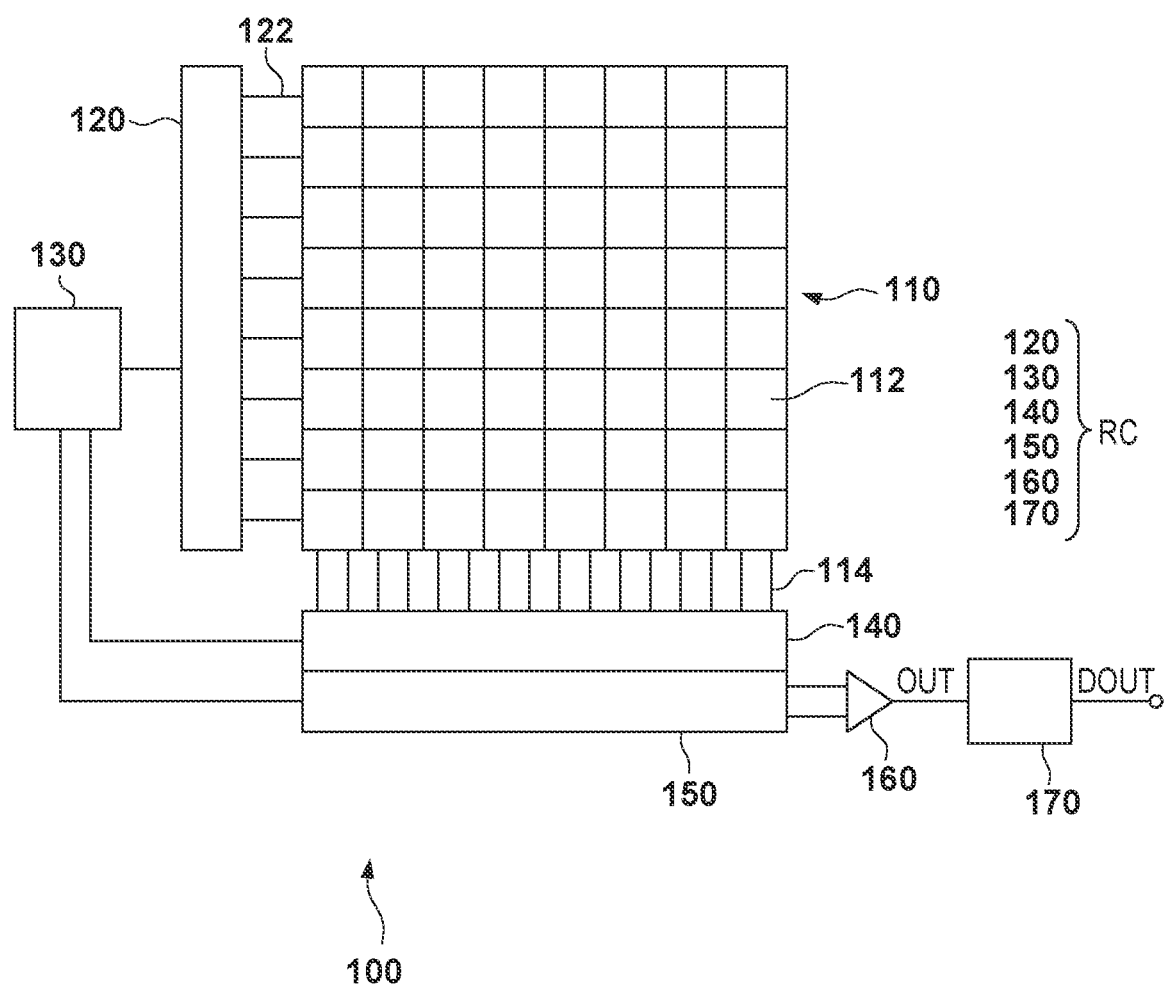
FIG. 2 is a view showing an example of the arrangement of an imaging unit.

FIG. 2 shows an example of the arrangement of the imaging unit 100. As described above, the imaging unit 100 includes the pixel array 110 including a plurality of pixels 112 and a readout circuit RC that reads out signals from the plurality of pixels 112 of the pixel array 110. The plurality of pixels 112 can be arrayed to form a plurality of rows and a plurality of columns. The readout circuit RC can include a row selection circuit 120, a timing generator (this can also be referred to as a control unit or state machine) 130, a buffer circuit 140, a column selection circuit 150, an amplifier circuit 160, and an AD converter 170.

The row selection circuit 120 selects a row of the pixel array 110. The row selection circuit 120 can be arranged to select a row by driving a row control signal 122. The buffer circuit 140 buffers signals from the pixels 112 of one of the plurality of rows of the pixel array 110 which is selected by the row selection circuit 120. The buffer circuit 140 buffers the signals of a plurality of columns output to a plurality of column signal transmission paths 114 of the pixel array 110. Each column signal transmission path 114 includes a first signal line and a second column signal line which form a column signal line pair. A noise level (at the time of a normal mode to be described later) of the pixel 112 or a radiation signal (at the time of an extension mode to be described later) corresponding to the radiation detected in the pixel 112 can be output to the first column signal line. A radiation signal corresponding to the radiation detected in the pixel 112 can be output to a second column signal line 322. The buffer circuit 140 can include an amplifier circuit.

The column selection circuit 150 selects, in a predetermined order, signal pairs of one row buffered by the buffer circuit 140. The amplifier circuit 160 amplifies the signal pairs selected by the column selection circuit 150. In this case, the amplifier circuit 160 can be arranged as a differential amplifier that amplifies the difference of a signal pair (two signals). The AD converter 170 can include the AD converter 170 that A/D-converts a signal OUT output from the amplifier circuit 160 and outputs a digital signal DOUT (a radiation image signal).

Figure 3:
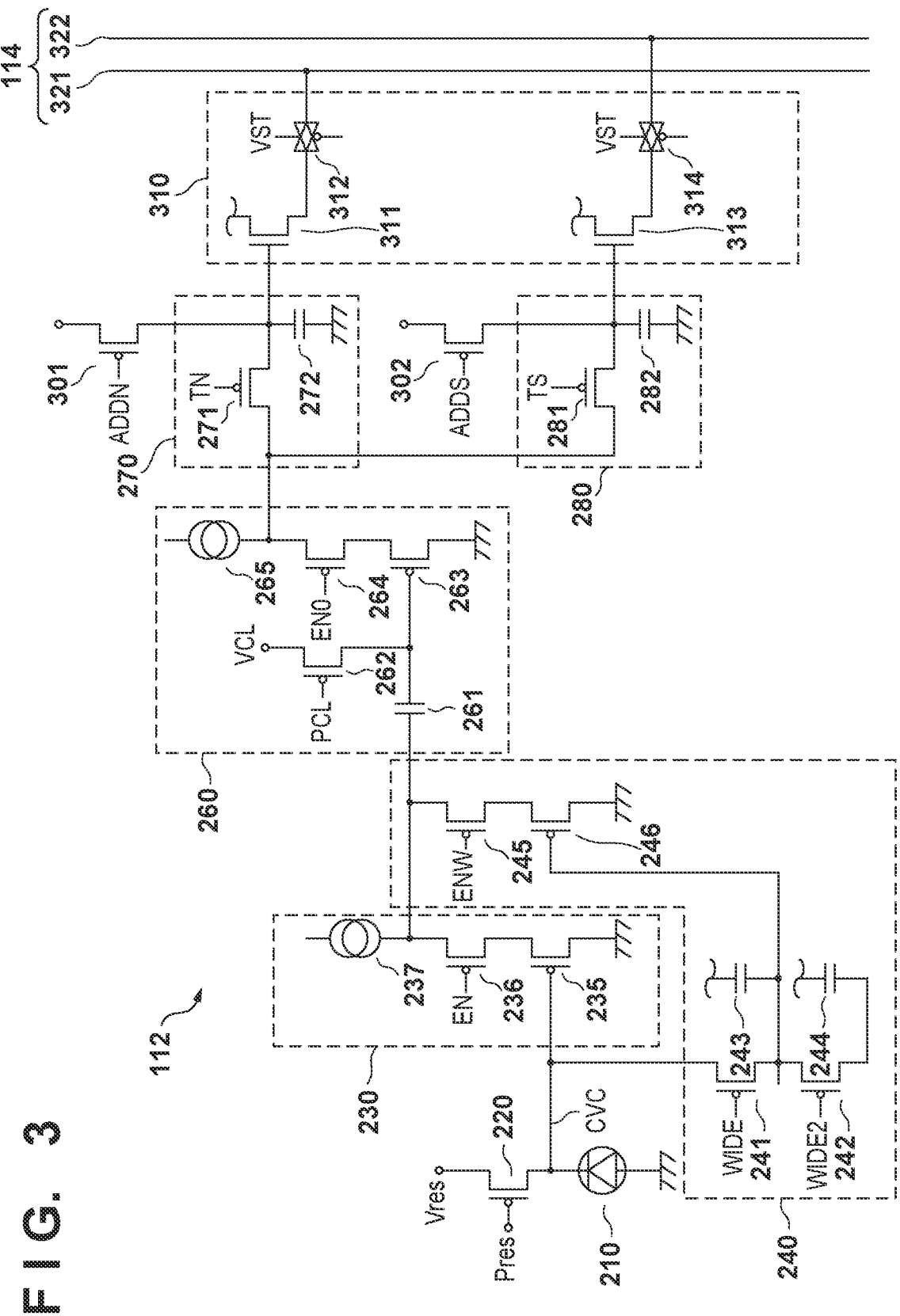
FIG. 3 is a circuit diagram showing an example of the arrangement of one pixel.

FIG. 3 shows an example of the arrangement of one pixel 112. The pixel 112 includes, for example, a conversion element 210, a reset switch 220 (reset unit), an amplifier circuit 230, a sensitivity changing unit 240, a clamp circuit 260, sample and hold circuits (holding portions) 270 and 280, and an output circuit 310. Each pixel 112 has the normal mode and the extension mode as the modes concerning the imaging method. The extension mode is a mode for obtaining a radiation image in accordance with the energy subtraction method.

The conversion element 210 converts radiation into an electrical signal. The conversion element 210 can be formed by, for example, a scintillator that can be shared by the plurality of pixels and a photoelectric conversion element. The conversion element 210 includes a charge accumulation portion that accumulates a converted electrical signal (charges), that is, an electrical signal corresponding to radiation. The charge accumulation portion is connected to the input terminal of the amplifier circuit 230.

The amplifier circuit 230 can include MOS transistors 235 and 236, and a current source 237. The MOS transistor 235 is connected to the current source 237 via the MOS transistor 236. The MOS transistor 235 and the current source 237 form a source follower circuit. The MOS transistor 236 is an enable switch which is turned on by activating an enable signal EN, and sets the source follower circuit formed by the MOS transistor 235 and the current source 237 in an operation state.

The charge accumulation portion of the conversion element 210 and the gate of the MOS transistor 235 function as a charge/voltage conversion unit CVC that converts charges accumulated in the charge accumulation portion into a voltage. That is, a voltage V (=Q/C) determined by charges Q accumulated in the charge accumulation portion and a capacitance value C of the charge/voltage conversion unit appears in the charge/voltage conversion unit CVC. The charge/voltage conversion unit CVC is connected to a reset potential Vres via the reset switch 220. When a reset signal PRES is activated, the reset switch 203 is turned on, and the potential of the charge/voltage conversion unit is reset to the reset potential Vres. The reset switch 220 can include a transistor that has the first main electrode (drain) connected to the charge accumulation portion of the conversion element 210, the second main electrode (source) to which the reset potential Vres is applied, and a control electrode (gate). The transistor electrically connects the first main electrode and the second main electrode by receiving an ON voltage at the control electrode, and resets the charge accumulation portion of the conversion element 210.

The clamp circuit 260 clamps, by a clamp capacitor 261, a reset noise level output from the amplifier circuit 230 in accordance with the potential of the reset charge/voltage conversion unit CVC. The clamp circuit 260 is a circuit configured to cancel the reset noise level from a signal (radiation signal) output from the amplifier circuit 230 in accordance with charges (electrical signal) converted by the conversion element 210. The reset noise level includes kTC noise at the time of reset of the charge/voltage conversion unit CVC. A clamp operation is performed by turning on a MOS transistor 262 by activating a clamp signal PCL, and then turning off the MOS transistor 262 by deactivating the clamp signal PCL.

The output side of the clamp capacitor 261 is connected to the gate of a MOS transistor 263. The source of the MOS transistor 263 is connected to a current source 265 via a MOS transistor 264. The MOS transistor 263 and the current source 265 form a source follower circuit. The MOS transistor 264 is an enable switch which is turned on by activating an enable signal EN0 supplied to its gate, and sets the source follower circuit formed by the MOS transistor 263 and the current source 265 in an operation state.

The output circuit 310 includes MOS transistors 311, 313, and 315 and row selection switches 312 and 314. The MOS transistors 311, 313, and 315, respectively, form source follower circuits with current sources (not shown) connected to column signal lines 321 and 322.

The sample and hold circuit 280 can sample and hold (hold) a radiation signal as a signal output from the clamp circuit 260 in accordance with charges generated in the conversion element 210. The sample and hold circuit 280 can include a switch 281 and a capacitor 282. The switch 281 is turned on by activating a sample and hold signal TS. The radiation signal output from the clamp circuit 260 is written in the capacitor 282 via the switch 281 by activating the sample and hold signal TS.

In the normal state in which the reset switch 220 resets the potential of the charge/voltage conversion unit CVC, and the MOS transistor 262 is ON, the clamp circuit 260 outputs the noise level (offset component) of the clamp circuit 260. The sample and hold circuit 270 can sample and hold (hold) the noise level of the clamp circuit 260. The sample and hold circuit 270 can include a switch 271 and a capacitor 272. The switch 271 is turned on by activating a sample and hold signal TN. A noise level output from the clamp circuit 260 is written in the capacitor 272 via the switch 271 by activating the sample and hold signal TN. In the extension mode, the sample and hold circuit 270 can also be used to hold a radiation signal as a signal output from the clamp circuit 260 in accordance with charges generated in the conversion element 210.

When row selection signals VST are activated, signals corresponding to signals held by the sample and hold circuits 270 and 280 are output to the first column signal line 321 and the second column signal line 322 that form the column signal transmission paths 114. More specifically, a signal N corresponding to a signal (a noise level or a radiation signal) held by the sample and hold circuit 270 is output to the column signal line 321 via the MOS transistor 311 and the row selection switch 312. A signal S corresponding to a signal held by the sample and hold circuit 280 is output to the column signal line 322 via the MOS transistor 313 and the row selection switch 314.

The pixel 112 may include addition switches 301 and 302 configured to add signals of the plurality of pixels 112. In an addition mode, addition mode signals ADDN and ADDS are activated. The capacitors 272 of the plurality of pixels 112 are connected to each other by activating the addition mode signal ADDN, averaging the signals (noise level or radiation signal). The capacitors 282 of the plurality of pixels 112 are connected to each other by activating the addition mode signal ADDS, averaging the radiation signals.

The pixel 112 can include the sensitivity changing unit 240. The sensitivity changing unit 240 can include switches 241 and 242, capacitors 243 and 244, and MOS transistors 245 and 246. When a first change signal WIDE is activated, the switch 241 is turned on, and the capacitance value of the first additional capacitor 243 is added to the capacitance value of the charge/voltage conversion unit CVC. Consequently, the sensitivity of the pixel 112 is decreased. Further, when a second change signal WIDE2 is also activated, the switch 242 is also turned on, and the capacitance value of the second additional capacitor 244 is added to the capacitance value of the charge/voltage conversion unit CVC. Consequently, the sensitivity of the pixel 112 is further decreased. A dynamic range can be widened by adding a function of decreasing the sensitivity of the pixel 112. An enable signal ENW may be activated when the first change signal WIDE is activated. In this case, the MOS transistor 246 performs a source follower operation. Note that when the switch 241 of the sensitivity changing unit 240 is turned on, the potential of the charge accumulation portion of the conversion element 210 may be changed by charge redistribution. Consequently, some signals may be destructed.

The above-described reset signal Pres, enable signal EN, clamp signal PCL, enable signal EN0, sample and hold signals TN and TS, and row selection signals VST are control signals controlled by the row selection circuit 120 and correspond to the row control signals 122 of FIG. 2.

In the pixel 112 having the arrangement as shown in FIG. 3, signals are not destructed in, for example, the charge accumulation portion of the conversion element 210 in a sample and hold operation. That is, in the pixel 112 having the arrangement as shown in FIG. 3, the radiation signals can be nondestructively read out. Such an arrangement is advantageous to radiation imaging to which the energy subtraction method is applied to be described below.

The extension mode for obtaining a radiation image in accordance with the energy subtraction method will be described below. The extension mode can include the following three sub-modes (extension modes 1, 2, and 3).

Figure 4:
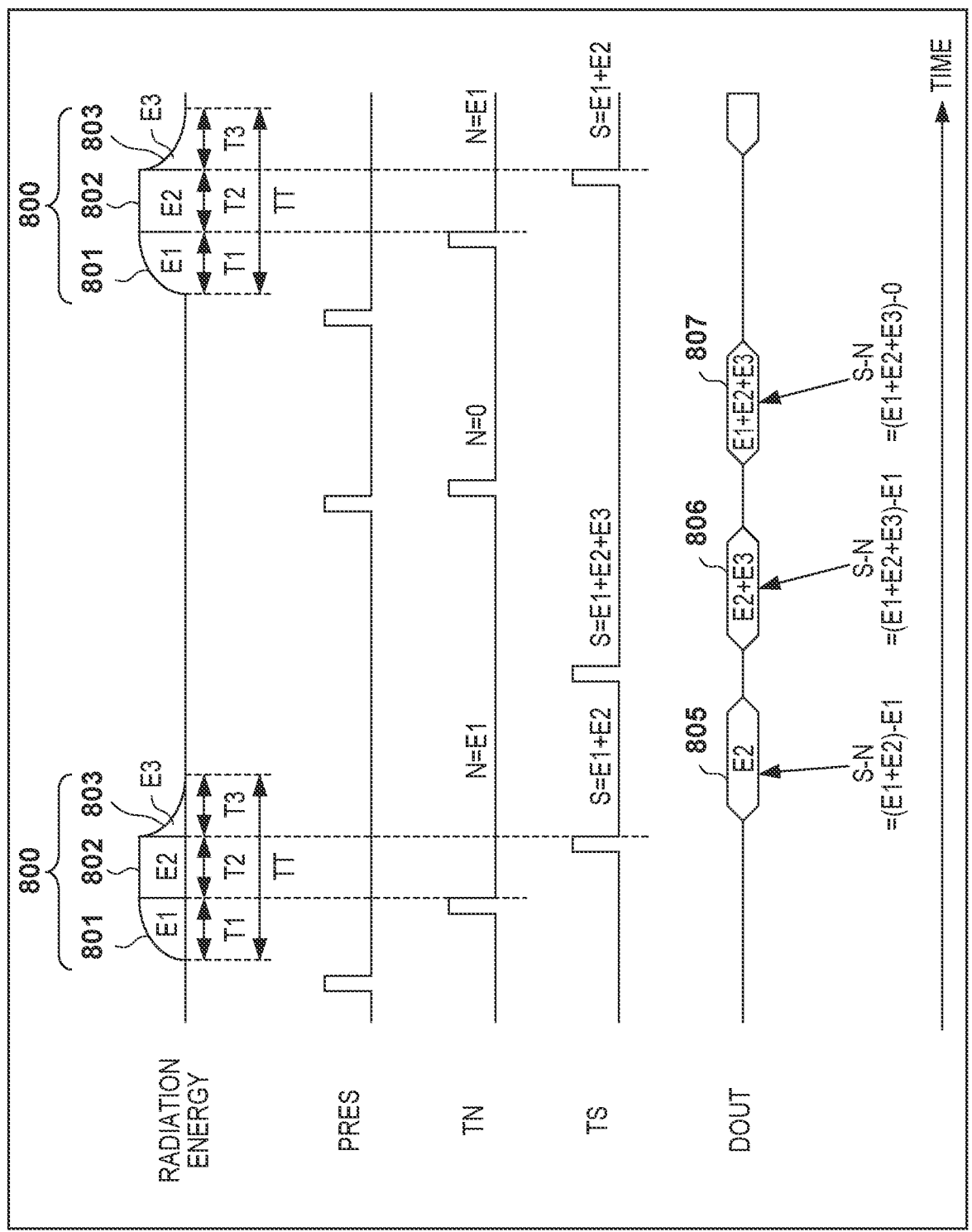
FIG. 4 is a timing chart showing an example of the operation of the radiation imaging apparatus in extension mode 1.

FIG. 4 shows the operation of the radiation imaging apparatus 1 in extension mode 1. In FIG. 4, the abscissa indicates a time. "Radiation energy" is energy of radiation which is emitted from the radiation source 400 and irradiates the imaging unit 100. "PRES" is the reset signal RPES. "TS" is the sample and hold signal TS. "DOUT" is an output of the A/D convertor 170. The control apparatus 350 can control synchronization of radiation emission from the radiation source 400 and the operation of the imaging unit 100. The timing generator 130 controls an operation in the imaging unit 100. The clamp signal PCL is also activated over a predetermined period in a period during which the reset signal PRES is activated, and the clamp circuit 260 clamps a noise level.

As shown in the example of FIG. 4, the energy (wavelength) of radiation 800 emitted from the radiation source 400 changes in the radiation period of the radiation. This is caused by the blunt leading and trailing edges of the tube voltage of the radiation source 400. For this reason, assume that the radiation 800 is made from radiation 801 in a leading period, radiation 802 in a stable period, and radiation 803 in a trailing period. Energy E1 of the radiation 801, energy E2 of the radiation 802, and energy E3 of the radiation 803 can be different from each other. By using this, a radiation image according to the energy subtraction method can be obtained.

In an irradiation period (a first period TT) of the radiation 800, the conversion element 210 of each pixel 112 is not reset (the reset signal Pres). In the irradiation period (the first period TT) of the radiation 800, an electrical signal (charges) obtained upon the incident radiation can be kept accumulated in the conversion element 210. In the irradiation period (the first period TT) of the radiation 800, since the conversion element 210 of each pixel 112 is not reset, it is advantageous in reducing the irradiation of the radiation which does not contribute to the imaging and obtaining a radiation image for the energy subtraction method within a shorter time.

Before emission (irradiation for the imaging unit 100) of the radiation 800, the reset signal PRES is activated for a predetermined period and accordingly the conversion element 210 is reset. At this time, the clamp signal PCL is also activated for the predetermined period, and the clamp circuit 260 is clamped to the reset level (the noise level).

After the reset signal PRES is activated for the predetermined period, the radiation is emitted from the radiation source 400 in accordance with an exposure command from the exposure control apparatus 300 to the radiation source 400. This operation is performed as follows as an example. First, the exposure switch of the exposure control apparatus 300 is turned on, and the exposure control apparatus 300 notifies the control apparatus 350 of the turn-on operation. In response to this, a command is output from the control apparatus 350 to the imaging unit 100 to start a series of operations (to be referred to as an imaging sequence) for imaging. The imaging unit 100 activates the reset signal PRES for the predetermined period as the start operation of the imaging sequence. Next, in response to the start of the imaging sequence of the imaging unit 100, the control apparatus 350 outputs a command for starting the radiation emission to the radiation source 400 via the exposure control apparatus 300. In response to this, the radiation source 400 starts radiation emission.

When the predetermined period has elapsed upon activation of the reset signal PRES for the predetermined period, the sample and hold signal TN is activated for the predetermined period. Accordingly, upon reception of irradiation of the radiation 801 having the energy E1, a signal (E1) corresponding to an electrical signal generated by the conversion element 210 of the pixel 112 of the pixel array 110 is sampled and held by the sample and hold circuit 270.

When the predetermined period has elapsed upon activation of the sample and hold signal TN for the predetermined period, the sample and hold signal TS is activated for the predetermined period. Accordingly, upon reception of irradiation of the radiation 801 having the energy E1 and the radiation 802 having the energy E2, a signal (E1+E2) corresponding to an electrical signal generated by the conversion element 210 of the pixel 112 of the pixel array 110 is sampled and held by the sample and hold circuit 280.

Next, a signal corresponding to the difference between the signal (E1) sampled and held by the sample and hold circuit 270 and the signal (E1+E2) sampled and held by the sample and hold circuit 280 is output from the readout circuit RC as a first signal 805. Referring to FIG. 4, "N" indicates a signal sampled and held by the sample and hold circuit 270 and output to the first column signal line 321, and "S" indicates a signal sampled and held by the sample and hold circuit 280 and output to the second column signal line 322.

When the predetermined period has elapsed upon activation of the sample and hold signal TS for the predetermined period (upon completion of irradiation (irradiation of the radiation 800) of the radiation 803 having the energy E3), the sample and hold signal TS is activated for the predetermined period again. Accordingly, upon reception of irradiation of the radiation 801 having the energy E1, the radiation 802 having the energy E2, and the radiation 803 having the energy E3, a signal (E1+E2+E3) corresponding to an electrical signal generated by the conversion element 210 of the pixel 112 of the pixel array 110 is sampled and held by the sample and hold circuit 280.

Next, a signal corresponding to the difference between the signal (E1) sampled and held by the sample and hold circuit 270 and the signal (E1+E2+E3) sampled and held by the sample and hold circuit 280 is output from the readout circuit RC as a second signal 806.

Next, the reset signal PRES is activated for the predetermined period, and then the sample and hold signal TN is activated for the predetermined period. Accordingly, the reset level (0) is sampled and held by the sample and hold circuit 270. Next, a signal corresponding to the difference between the signal (0) sampled and held by the sample and hold circuit 270 and the signal (E1+E2+E3) sampled and held by the sample and hold circuit 280 is output from the readout circuit RC as a third signal 807.

By repeating the above operation a plurality of times, radiation images of a plurality of frames (that is, a moving image) are obtained.

The signal processing unit 352 can obtain the first signal 805 (E2), the second signal 806 (E2+E3), and the third signal 807 (E1+E2+E3) as described above. The signal processing unit 352 can obtain an irradiation amount e1 of the radiation 801 having the energy E1, an irradiation amount e2 of the radiation 802 having the energy E2, and an irradiation amount e3 of the radiation 803 having the energy E3 based on the first signal 805, the second signal 806, and the third signal 807. More specifically, the signal processing unit 352 calculates a difference ((E2+E3)−E2) between the first signal 805 (E2) and the second signal (E2+E3) to obtain the irradiation amount e3 of the radiation 803 having the energy E3. The signal processing unit 352 calculates a difference ((E1+E2+E3)−(E2+E3)) between the second signal 806 (E2+E3) and the third signal (E1+E2+E3) to obtain the irradiation amount e1 of the radiation 801 having the energy E1. The first signal 805 (E2) indicates the irradiation amount e2 of the radiation 802 having the energy E2.

Therefore, the signal processing unit 352 obtains the radiation image by the energy subtraction method based on the irradiation amount e1 of the radiation 801 having the energy E1, the irradiation amount e2 of the radiation 802 having the energy E2, and the irradiation amount e3 of the radiation 803 having the energy E3.

Generation of the radiation image by the energy subtraction method which can be executed by the signal processing unit 352 will be described below. FIG. 5A shows changes in time of an operation of FIG. 4 performed a plurality of times (estimated values ("estimated tube voltages") of the tube voltages of the radiation source 400 which are estimated based on the energies E1, E2, and E3 obtained in the radiation imaging apparatus 1 upon execution of the operation for a plurality of frames. The estimated values corresponding to the energies E1, E2, and E3 are indicated by E1, E2, and E3. FIG. 5B shows changes in time of an operation of FIG. 4 performed a plurality of times (estimated values ("estimated dose") of the dose of the radiation source 400 which are estimated based on the energies E1, E2, and E3 obtained in the radiation imaging apparatus 1 upon execution of the operation for a plurality of frames. The estimated values corresponding to the energies E1, E2, and E3 are indicated by E1, E2, and E3. Large changes in tube voltage and radiation dose are obvious between the frames from FIGS. 5A and 5B.

The cause for this may be considered based on a variation in time from transmission of a dose command from the exposure control apparatus 300 to the radiation source 400 to the start of emission of the radiation from the radiation source 400. By this variation, a period T1 (see FIG. 4) from the start of irradiation of the radiation 800 to the completion of the sampling and holding of the sample and hold circuit 270 varies. In addition, a period (T1+T2) (see FIG. 4) from the start of the irradiation of the radiation 800 to the completion of the sampling and holding of the sample and hold circuit 280 can also vary. As a result, the values of the first signal 805 (E2) and the second signal 806 (E2+E3) vary between the frames.

Even if the period T1 varies, the start time of the period T2 accordingly shifts, but the length of a period T2 itself does not shift. Even if the period T1 varies, the irradiation amount e2 of the radiation 802 having the energy E2 detected by the radiation imaging apparatus 1 has a small error. If the period T1 becomes long, a period T3 becomes short. If the period T1 becomes short, the period T3 becomes long. Accordingly, even if the period T1 varies, the sum of the irradiation amounts e1 and e3 of the radiations 802 having the energies E1 and E3 detected by the radiation imaging apparatus 1 has a small error.

Figure 6A:
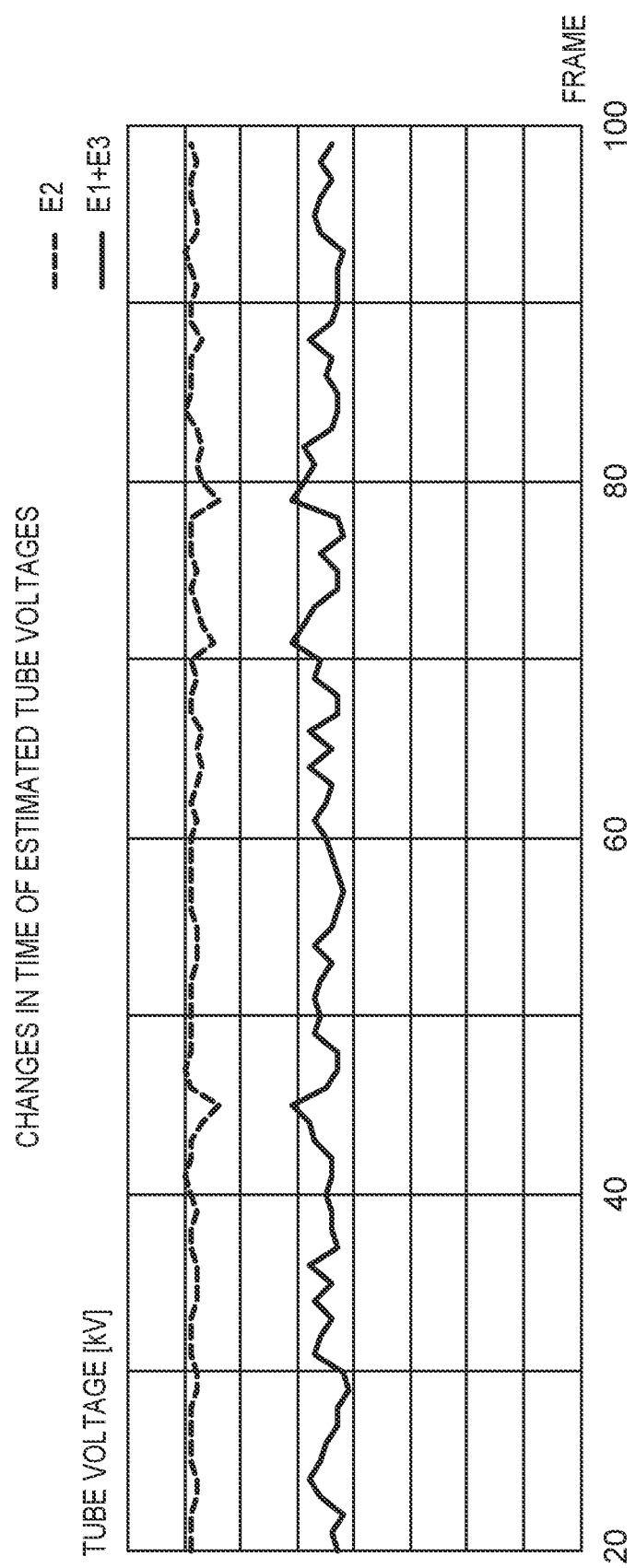
FIG. 6A is a graph for explaining an effect of reducing a variation between the frames of a radiation image.
Figure 6B:
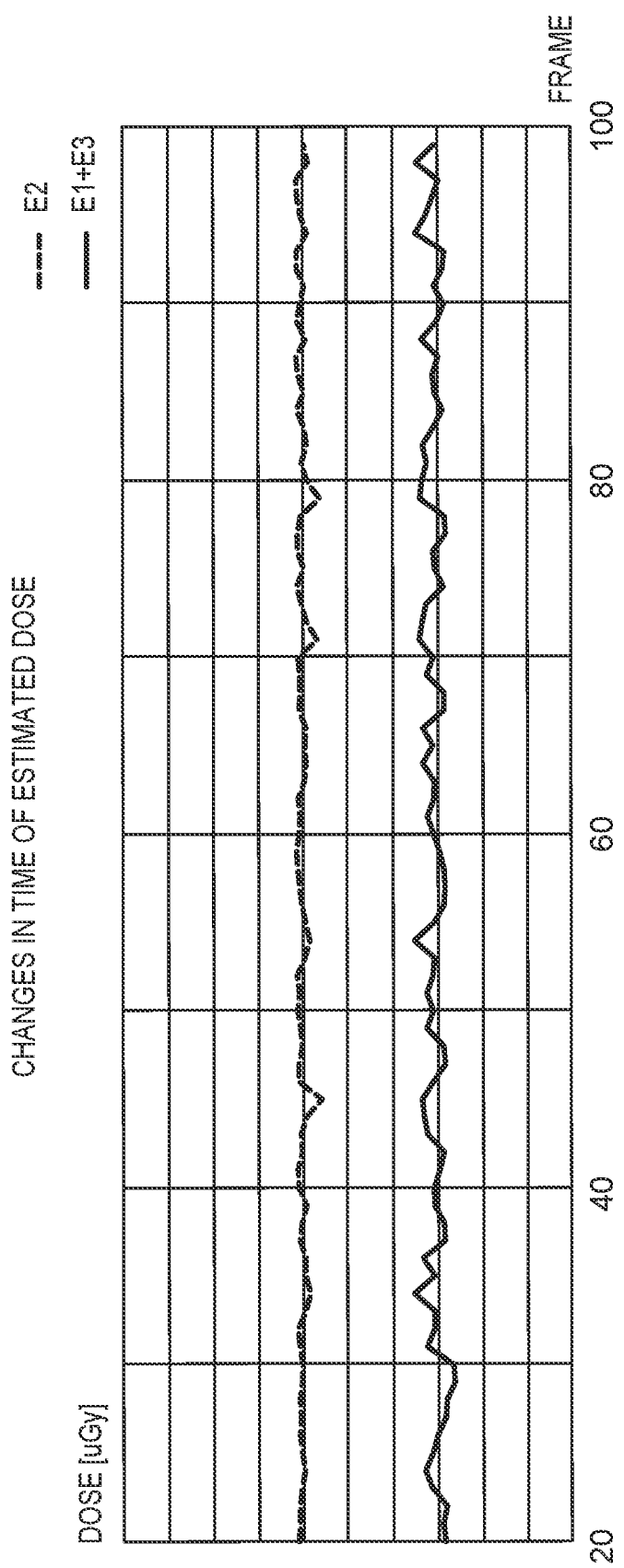
FIG. 6B is a graph for explaining an effect of reducing a variation between the frames of a radiation image.

This can also be supported from FIGS. 6A and 6B. FIG. 6A shows the estimated values of the tube voltages corresponding to the energy E2 and the energy E1+E3. FIG. 6B shows the estimated values of the radiation doses corresponding to the energy E2 and the energy E1+E3. As for the energy E2 and the energy E1+E3, the variation between the frames of the radiation image is obviously small from FIGS. 6A and 6B.

Judging from the above description, the image (the second image) of the irradiation amount e2 and the image (the third image) of the irradiation amount e1+e3 can be said to be images having small variations. Generation of a new radiation image by the energy subtraction method based on the image (the second image) of the irradiation amount e2 and the image (the third image) of the irradiation amount e1+e3 is preferable. The image (the third image) of the irradiation amount e1+e3 can be obtained by calculating a difference between the image (the third image=the third signal 807) of the irradiation amount e1+e2+e3 and the image (the second image=the first signal 805) of the irradiation amount e2. The image (the first image=the third signal 807) of the irradiation amount e1+e2+e3 is an image corresponding to an electrical signal generated by the conversion element 210 of each of the plurality of pixels 112 in the first period TT (whole) serving as the irradiation period of the radiation 800. The image (the second image=the first signal 805) of the irradiation amount e2 is an image corresponding to an electrical signal generated by the conversion element 210 of each of the plurality of pixels 112 in the second period T2 which starts after the start of the first period TT and ends before the end of the first period TT.

The energy subtraction method can be selected from various methods. For example, it is possible, by calculating a difference between the radiation image of the first energy and the radiation image of the second energy, to obtain a bone image and a soft tissue image. The bone image and the soft tissue image may be generated by solving nonlinear simultaneous equations based on the radiation image of the first energy and the radiation image of the second energy. It is also possible to obtain a contrast medium image and the soft tissue image based on the radiation image of the first energy and the radiation image of the second energy. It is also possible to obtain an electron density image and an effective atomic number image based on the radiation image of the first energy and the radiation image of the second energy.

In the above example, a plurality of images having different energies are obtained by using the blunt leading and trailing edges of the tube voltage of the radiation source 400, and a new radiation image is formed based on the plurality of images. The plurality of images can be obtained by intentionally adjusting the waveform of the tube voltage of the radiation source 400. Alternatively, the plurality of images may be obtained by emitting radiation having a wide energy band (wavelength band) from the radiation source 400 and changing the energy of the radiation by changing a plurality of filters.

Figure 7:
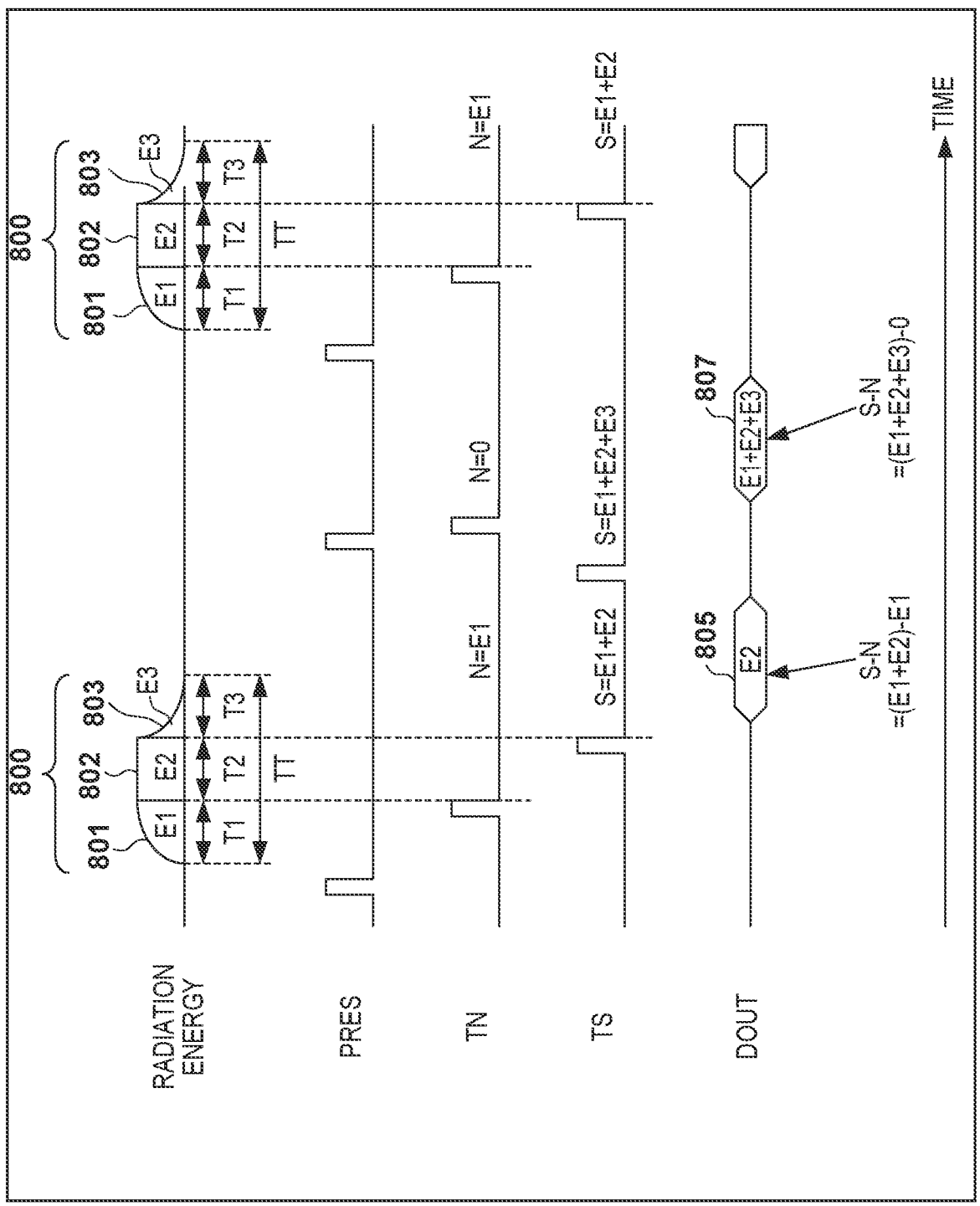
FIG. 7 is a timing chart showing an example of the operation of the radiation imaging apparatus in an extension mode 2.

FIG. 7 shows the operation of the radiation imaging apparatus 1 in extension mode 2. In extension mode 1, the second signal 806 (E2+E3) is output from the readout circuit RC. However, if the signal processing unit 352 does not require the second signal 806 (E2+E3), it is advantageous in improving the frame rate unless the readout circuit RC outputs the second signal 806 (E2+E3). In extension mode 2, the readout circuit RC outputs the first signal 805 (E2) and the signal 807 (E1+E2+E3), but does not output the third signal second signal 806 (E2+E3).

The operation of the radiation imaging apparatus 1 in extension mode 2 will be described below. When the predetermined period has elapsed upon activation of the reset signal PRES for the predetermined period, the sample and hold signal TN is activated for the predetermined period. Accordingly, a signal (E1) corresponding to an electrical signal generated by the conversion element 210 of each pixel 112 of the pixel array 110 upon reception of irradiation of the radiation 801 having the energy E1 is sampled and held by the sample and hold circuit 270.

When the predetermined period has elapsed after the sample and hold signal TN is activated for the predetermined period, the sample and hold signal TS is activated for the predetermined period. Accordingly, upon reception of the irradiation of the radiation 801 having the energy E1 and the radiation 802 having the energy E2, a signal (E1+E2) corresponding to an electrical signal generated by the conversion element 210 of each pixel 112 of the pixel array 110 is sampled and held by the sample and hold circuit 280.

Next, a signal corresponding to the difference between the signal (E1) sampled and held by the sample and hold circuit 270 and the signal (E1+E2) sampled and held by the sample and hold circuit 280 is output from the readout circuit RC as the first signal 805.

When the predetermined period of time has elapsed after the sample and hold signal TS is activated for the predetermined period (after the end of irradiation (irradiation of the radiation 800) of the radiation 803 having the energy E3), the sample and hold signal TS is activated for the predetermined period again. Accordingly, upon reception of the radiations 801, 802, and 803 having the energies E1, E2, and E3, a signal (E1+E2+E3) corresponding to an electrical signal generated by the conversion element 210 of each pixel 112 of the pixel array 110 is sampled and held by the sample and hold circuit 280.

Next, the reset signal PRES is activated for the predetermined period, and then the sample and hold signal TN is activated for the predetermined period. Accordingly, the reset level (0) is sampled and held by the sample and hold circuit 270. Next, a signal corresponding to the difference between the signal (the reset level=0) sampled and held by the sample and hold circuit 270 and the signal (E1+E2+E3) sampled and held by the sample and hold circuit 280 is output from the readout circuit RC as the third signal 807.

By repeating the above operation a plurality of times, radiation images of a plurality of frames (that is, a moving image) are obtained.

FIG. 8 shows the operation of the radiation imaging apparatus 1 in extension mode 3. In extension mode 3, the second period T2 is determined based on a synchronization signal DET representing the start of radiation irradiation for the radiation imaging apparatus 1. More specifically, in extension mode 3, in response to the synchronization signal DET, the timing generator 130 controls the timing for causing the row selection circuit 120 to activate the sample and hold signals TN and TS, thereby determining the second period T2.

Figure 9A:
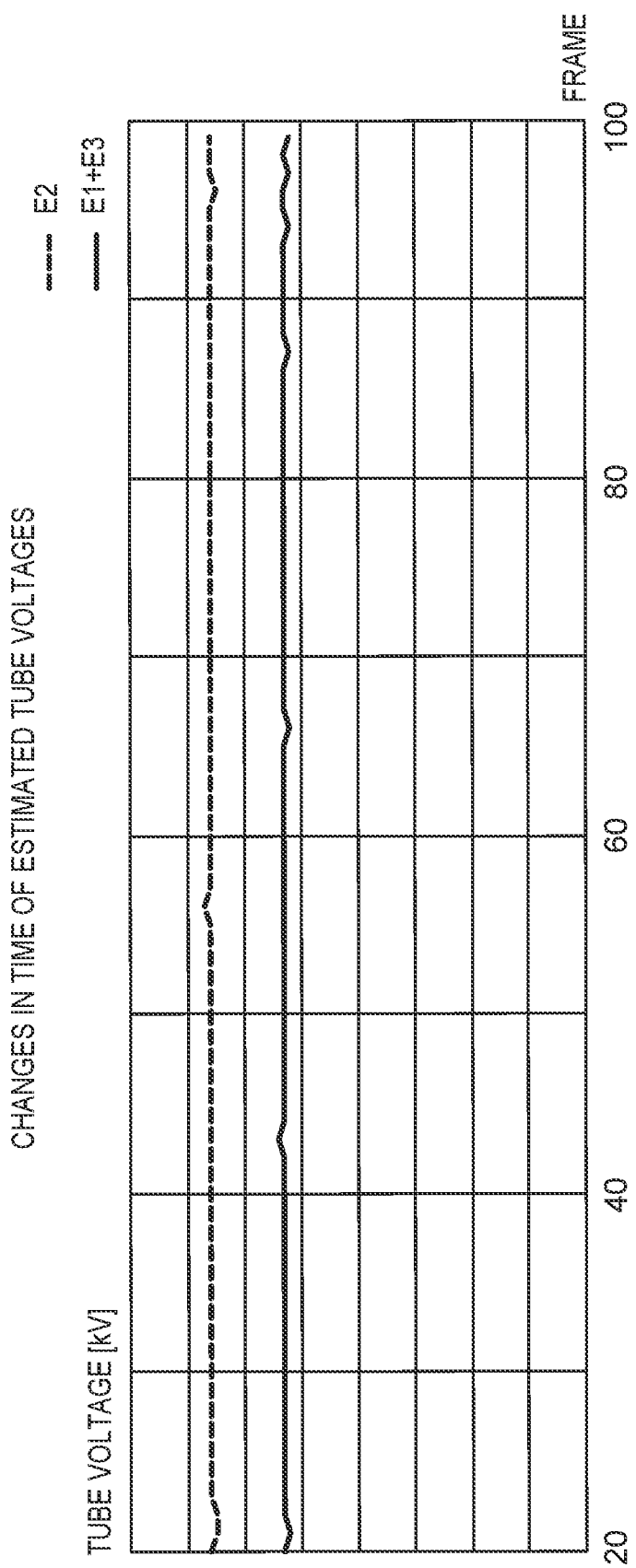
FIG. 9A is a graph for explaining an effect of reducing a variation between the frames of a radiation image.

FIG. 9A shows the estimated values of the tube voltages corresponding to the energies E2 and E1+E3. FIG. 9B shows the estimated values of radiation doses corresponding to the energies E2 and E1+E3. By controlling the sampling and holding based on the synchronization signal DET, variations between the frames of the radiation image for the energies E2 and E1+E3 are obviously small from FIGS. 9A and 9B.

The synchronization signal DET can be generated by various methods. For example, a measurement unit for measuring the tube current can be arranged in the radiation source 400. If the measured tube current exceeds a threshold, the synchronization signal DET indicating the start of the radiation irradiation can be activated. In this case, the imaging unit 100 receives the synchronization signal DET. Alternatively, the imaging unit 100 causes the readout circuit RC to periodically read out the signal from one or the plurality of conversion elements 210, and the synchronization signal DET is generated based on the readout signal. Alternatively, a sensor for detecting the radiation irradiation may be arranged in the imaging unit 100, and the synchronization signal DET may be generated based on the output from the sensor.

In extension mode 3, the operation for the variation in time from transmission of the dose command from the exposure control apparatus 300 to the radiation source 400 to the start of radiation emission from the radiation source 400 becomes insensitive, and a more accurate radiation image can be obtained.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
an imaging unit including a pixel array having a plurality of pixels, each of the plurality of pixels including a conversion element configured to convert radiation into an electrical signal and a reset unit configured to reset the conversion element; and
a signal processing unit configured to process a signal from the imaging unit,
the signal processing unit being configured to generate a radiation image in a first period based on a first image corresponding to an electrical signal converted by the conversion unit of each of the plurality of pixels, and to generate in a second period included within the first period a second image corresponding to an electrical signal converted by the conversion element of each of the plurality of pixels, wherein
the reset unit is configured not to reset the conversion element in the plurality of pixels in the first period.

2. The radiation imaging apparatus according to claim 1, wherein the signal processing unit is configured to generate a third image by calculating a difference between the first image and the second image, and to generate a radiation image based on the second image and the third image.

3. The radiation imaging apparatus according to claim 2, wherein the signal processing unit is configured to generate a radiation image based on a difference between the second image and the third image.

4. The radiation imaging apparatus according to claim 2, which is configured to nondestructively read out a signal corresponding to an electrical signal converted by the conversion element from each of the plurality of pixels.

5. The radiation imaging apparatus according to claim 4, wherein each of the plurality of pixels includes a sample and hold circuit configured to sample and hold an electrical signal converted by the conversion element, and
said radiation imaging apparatus is configured to nondestructively read out a signal corresponding to the electrical signal sampled and held by the sample and hold circuit.

6. The radiation imaging apparatus according to claim 4, wherein the imaging unit is configured to output a first signal nondestructively read out from each of the plurality of pixels in accordance with an electrical signal converted by the conversion element of each of the plurality of pixels in the second period, a second signal nondestructively read out from each of the plurality of pixels in accordance with an electrical signal converted by the conversion element of each of the plurality of pixels in a period from a start of the second period to the end of the first period, and a third signal nondestructively read out from each of the plurality of pixels in accordance with an electrical signal converted by the conversion element of each of the plurality of pixels in the entire first period, and
the signal processing unit is configured to obtain the second image and the third image based on the first signal, the second signal, and the third signal.

7. The radiation imaging apparatus according to claim 6, wherein the imaging unit includes a readout circuit configured to read out a signal from the pixel array, and
the readout circuit is configured to generate (i) the first signal based on a signal output from the pixel array in accordance with an electrical signal converted by the conversion element of each of the plurality of pixels in a period from the start of the first period to the start of the second period and a signal output from the pixel array in accordance with an electrical signal converted by the conversion element of each of the plurality of pixels in a period from the start of the first period to an end of the second period, (ii) generate the second signal based on a signal output from the pixel array in accordance with an electrical signal converted by the conversion element of each of the plurality of pixels in a period from the start of the first period to the start of the second period and a signal output from the pixel array in accordance with an electrical signal converted by the conversion element of each of the plurality of pixels in the entire first period, and (iii) generate the third signal based on a signal output from the pixel array in accordance with an electrical signal converted by the conversion element of each of the plurality of pixels in the entire first period.

8. The radiation imaging apparatus according to claim 4, wherein the imaging unit is configured to output a first signal nondestructively read out from each of the plurality of pixels in accordance with an electrical signal converted by the conversion element of each of the plurality of pixels in the second period and a third signal nondestructively read out from each of the plurality of pixels in accordance with an electrical signal converted by the conversion element of each of the plurality of pixels in the entire first period, and
the signal processing unit is configured to obtain the second image and the third image based on the first signal and the third signal.

9. The radiation imaging apparatus according to claim 8, wherein the imaging unit includes a readout circuit configured to read out a signal from the pixel array, and
the readout circuit is configured to generate (i) the first signal based on a signal output from the pixel array in accordance with an electrical signal converted by the conversion element of each of the plurality of pixels in a period from the start of the first period to a start of the second period and a signal output from the pixel array in accordance with an electrical signal converted by the conversion element of each of the plurality of pixels in a period from the start of the first period to an end of the second period, and (ii) generate the third signal based on a signal output from the pixel array in accordance with an electrical signal converted by the conversion element of each of the plurality of pixels in the entire first period.

10. The radiation imaging apparatus according to claim 1, wherein the second period is configured to be determined based on a synchronization signal indicating a start of radiation irradiation for the radiation imaging apparatus.

11. The radiation imaging apparatus according to claim 5, wherein the sample and hold circuit is configured to be controlled based on a synchronization signal indicating a start of radiation irradiation for the radiation imaging apparatus.

12. The radiation imaging apparatus according to claim 10, wherein the imaging unit is configured to detect radiation irradiation and generate the synchronization signal.

13. The radiation imaging apparatus according to claim 10, wherein the imaging unit is configured to receive the synchronization signal.

14. The radiation imaging apparatus according to claim 1, further comprising a radiation source.

15. A radiation imaging method for obtaining a radiation image using a radiation imaging apparatus including a plurality of pixels, each of the plurality of pixels including a conversion element configured to convert radiation into an electrical signal and a reset unit configured to reset the conversion element, comprising the steps of:
generating a radiation image based on a first image corresponding to an electrical signal converted by the conversion unit of each of the plurality of pixels in a first period; and
generating in a second period included within the first period a second image corresponding to an electrical signal converted by the conversion element of each of the plurality of pixels, wherein
the reset unit is configured not to reset the conversion element in the plurality of pixels, in the first period.

* * * * *